(12) United States Patent
Moulden et al.

(10) Patent No.: US 11,033,663 B2
(45) Date of Patent: Jun. 15, 2021

(54) TRAP BOTTLE ASSEMBLY FOR USE WITH MEDICAL SUCTION REGULATORS OR CONTROLLERS

(71) Applicant: Boehringer Technologies, LP, Phoenixville, PA (US)

(72) Inventors: Steven C. Moulden, West Chester, PA (US); Kevin P. Klocek, Wynnewood, PA (US)

(73) Assignee: Boehringer Technologies, LP, Phoenixville, PA (US)

( * ) Notice: Subject to any disclaimer, the term of this patent is extended or adjusted under 35 U.S.C. 154(b) by 281 days.

(21) Appl. No.: 16/295,483

(22) Filed: Mar. 7, 2019

(65) Prior Publication Data
US 2019/0298893 A1 Oct. 3, 2019

Related U.S. Application Data

(60) Provisional application No. 62/651,477, filed on Apr. 2, 2018.

(51) Int. Cl.
*A61M 1/00* (2006.01)
*A61J 1/14* (2006.01)
(Continued)

(52) U.S. Cl.
CPC ........ *A61M 1/0001* (2013.01); *A61J 1/1412* (2013.01); *A61M 1/0031* (2013.01); *A61J 1/1418* (2015.05); *A61J 1/1425* (2015.05); *A61M 1/0027* (2014.02); *A61M 16/0816* (2013.01); *A61M 39/1011* (2013.01); *A61M 2205/12* (2013.01); *A61M 2209/082* (2013.01)

(58) Field of Classification Search
CPC .............. A61M 1/0001; A61M 1/0031; A61M 1/0027; A61M 2209/082; A61M 1/0017; A61M 1/0011
USPC ....................................................... 604/319
See application file for complete search history.

(56) References Cited

U.S. PATENT DOCUMENTS 3,086,528 A * 4/1963 Eichelman ......... G05D 16/0655
604/540
3,855,997 A * 12/1974 Sauer ................. A61B 10/0045
600/573

(Continued)

FOREIGN PATENT DOCUMENTS

EP 0396029 B1 * 9/1992 ............ F16L 33/223
WO WO-2009063338 A1 * 5/2009 .......... A61M 1/0031

*Primary Examiner* — Tatyana Zalukaeva
*Assistant Examiner* — Eric Storr Sage Handberg
(74) *Attorney, Agent, or Firm* — Caesar Rivise, PC (57) ABSTRACT

A trap bottle assembly for mounting on a suction regulator or controller is disclosed. The trap bottle assembly includes a mounting adaptor for mounting on the suction regulator and a disposable trap bottle for releasable mounting on the mounting adaptor. The mounting adaptor includes a tubular connector and a body member having a peripheral sidewall from which a pair of pins extends. The threaded tubular connector connects the mounting adaptor to the suction regulator or controller. The trap bottle includes an annular flange for tightly engaging an undersurface of the body member to form a good fluid tight interface therebetween. The trap bottle includes a pair of recesses for receipt of the pair of pins, to enable the trap bottle to be releasably secured to the mounting adaptor.

10 Claims, 5 Drawing Sheets

(51) Int. Cl.
*A61M 39/10* (2006.01)
*A61M 16/08* (2006.01)

(56) References Cited

U.S. PATENT DOCUMENTS

| | | | | |
|---|---|---|---|---|
| 3,863,663 | A * | 2/1975 | Bornhorst | A61M 1/005 |
| | | | | 137/205 |
| 3,965,902 | A * | 6/1976 | Reilly | A61M 1/0001 |
| | | | | 604/320 |
| 4,513,875 | A * | 4/1985 | Kuehn, Sr. | B65D 11/06 |
| | | | | 206/509 |
| 5,363,860 | A * | 11/1994 | Nakao | A61M 1/0001 |
| | | | | 600/573 |
| 10,799,871 | B1 * | 10/2020 | Sternick | B01L 3/563 |
| 2007/0027433 | A1 * | 2/2007 | Garcia | A61M 1/0005 |
| | | | | 604/319 |

* cited by examiner

TRAP BOTTLE ASSEMBLY FOR USE WITH MEDICAL SUCTION REGULATORS OR CONTROLLERS

CROSS-REFERENCE TO RELATED APPLICATIONS

This utility application claims the benefit under 35 U.S.C. § 119(e) of Provisional Application Ser. No. 62/651,477 filed on Apr. 2, 2018 entitled Trap Bottle Assembly for Use with Medical Suction Regulators or Controllers. The entire disclosure of this provisional application is specifically incorporated by reference herein.

FIELD OF THE INVENTION

This invention relates generally to medical devices and more particularly to trap bottles assemblies for use with medical suction regulators or controllers, such as those for vacuum assisted venous drainage.

SPECIFICATION

Background of the Invention

Suction regulators or controllers are devices that are routinely used in hospitals to regulate the level of suction delivered from a central supply system to the patient. Patient safety requires the high vacuum from the central supply be regulated to a lower safe level and adjustable for any number of clinical needs. Suction is used to remove fluids and debris from body cavities and is employed in virtually any location where a patient is present. Modern hospitals employ central suction systems with distributed supply at the patient's bed via a wall connector and in other locations in the hospital, e.g., connected to a perfusion apparatus, such as a heart-lung machine located in an operating room. Mechanical suction regulators or controllers are connected to the distributed suction supply to reduce the high vacuum levels to lower levels safe for patients. Disposable canisters or other collection devices are typically used with suction regulators or controllers to accumulate fluids and debris. Such collection devices are typically located between the point of collection and the suction regulator or controller and serve to protect the piping system and manual controls from contamination by bodily substances.

Suction regulators or controllers are typically constructed to provide adjustable suction levels based on individual clinical requirements. Essential features for a suction regulator or controller include an inlet and outlet for attachment to the patient and a source of suction; a control mechanism for sensing changes in flow demand conditions and controlling the suction pressure output; a gauge for indicating the controlled output and specific and clinical safety measures that are specific to the type of suctioning to be performed.

While prior art suction regulators and fluid traps or canisters used therewith are generally suitable for their intended purposes they leave something to be desired from one or more the standpoints of simplicity of construction, ease of mounting, effectiveness of sealing, etc. The subject invention addresses those needs.

BRIEF SUMMARY OF THE INVENTION

One aspect of this invention is a trap bottle assembly for releasable mounting on a suction regulator or controller. The trap bottle assembly comprises a trap bottle and a mounting adaptor. The trap bottle is a hollow member has a bottom wall, and a peripheral side wall. The peripheral side wall has a top portion including a top surface from which an annular flange or lip projects upward at an acute angle. The annular flange or lip is configured to deflect or bend. The mounting adaptor is configured for releasable securement to a portion of the suction regulator or controller. The mounting adaptor comprises a body member in the form of a peripheral sidewall surrounding an undersurface of the body member. The peripheral sidewall is configured to receive and releasably mount the top portion of the sidewall of the trap bottle, whereupon the annular flange or lip of the trap bottle tightly engages the undersurface of the body member to cause the annular flange or lip of the trap bottle to deflect or bend and form a fluid tight interface between the undersurface of the body member and the annular flange or lip of the trap bottle.

In accordance with one preferred aspect of this invention the trap bottle assembly the body member includes a first pin projecting inward from the sidewall thereof. The first pin is configured for receipt within a first slot located at the top portion of the peripheral sidewall of the trap bottle to releasable mount the trap bottle to the mounting adaptor.

In accordance with another preferred aspect of this invention the trap bottle assembly includes a longitudinal central axis about which the peripheral sidewall of the trap bottle extends, and wherein the first slot comprises a first slot section extending parallel to the longitudinal central axis and a second slot section extending perpendicular to the longitudinal central axis. The first slot section is in communication with the second slot section. The first slot section is configured to receive the first pin and enable the trap bottle to be manipulated so that the first pin slides down the first slot section to the second slot section, whereupon rotation of the trap bottle about the longitudinal central axis causes the first pin to enter in the second slot section, thereby releasably mounting the trap bottle on the cap and connector assembly.

In accordance with another preferred aspect of this invention the body member of the mounting adaptor comprises a tubular connector having a peripheral sidewall surrounding a central passageway and external threads on the peripheral sidewall for receipt within an internally threaded bore in the suction regulator or controller to releasably mount the trap bottle assembly to the suction regulator or controller.

In accordance with another preferred aspect of this invention the body member of the cap and connector assembly includes bore for receipt of the tubular connector.

In accordance with another preferred aspect of this invention the tubular connector includes an inner end which is open to the central passageway. The inner end of the tubular connector is configured to be located adjacent the undersurface of the body member when the tubular connector is received within the bore of the body member of the cap and connector assembly.

In accordance with another preferred aspect of this invention the inner end of the tubular connector includes a slot into which a tool can be inserted to screw the tubular connector into the internally threaded bore of the suction regulator or controller to releasably mount the trap bottle assembly on the suction regulator or controller.

In accordance with another preferred aspect of this invention the body member of the mounting adaptor comprises a tubular connector having a peripheral sidewall surrounding a central passageway and external threads on the peripheral sidewall for receipt within an internally threaded bore in the suction regulator or controller to releasably mount the trap bottle assembly to the suction regulator or controller.

In accordance with another preferred aspect of this invention the suction regulator or controller includes a housing portion having an arcuate surface and a bore extending through the arcuate surface into the housing portion, and wherein the body member of the mounting adaptor includes a projection having a first arcuate recess therein. The first arcuate recess is configured to receive the arcuate surface of the housing portion when the trap bottle assembly is mounted on the suction regulator or controller.

In accordance with another preferred aspect of this invention the suction regulator or controller includes a knob projecting outward from the housing portion adjacent the arcuate surface and wherein the projection includes a second recess located adjacent the first arcuate recess. The second recess is configured to receive the knob when the trap bottle assembly is mounted on the suction regulator or controller.

BRIEF SUMMARY OF THE INVENTION

DETAILED DESCRIPTION OF THE PREFERRED EMBODIMENTS OF THE INVENTION

Figure 1A:
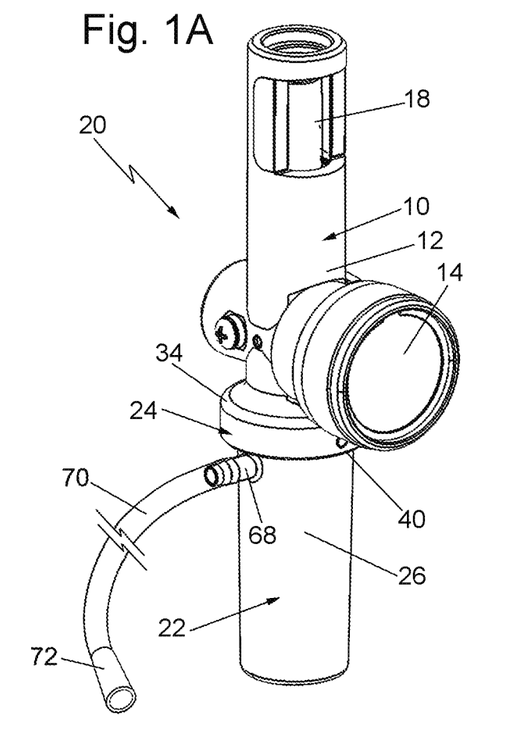
FIG. 1A is an isometric view of a conventional suction regulator or controller with a trap bottle assembly of the subject invention releasably mounted thereon and with conventional flexible tubing having a connector mounted on the trap bottle assembly.
Figure 1B:
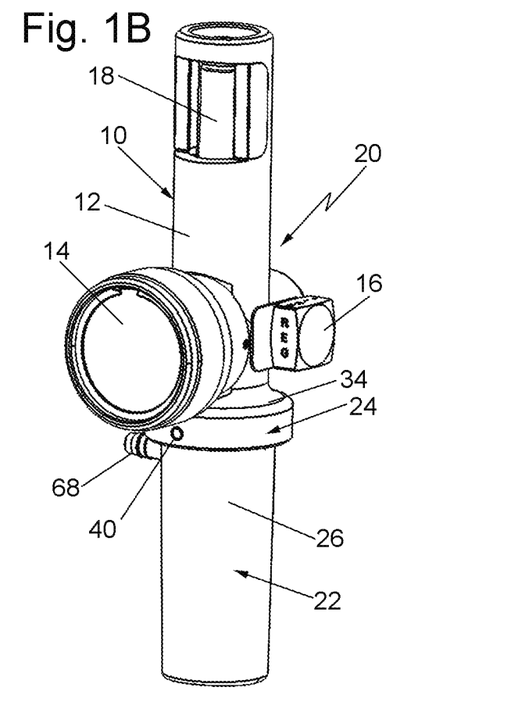
FIG. 1B is an isometric view of the suction regulator or controller with the trap bottle assembly of FIG. 1A mounted thereon, but taken from a different angle and with the flexible tubing and connector omitted in the interest of drawing simplicity.

Referring now to the various figures of the drawing wherein like reference characters refer to like parts, there is shown in FIG. 1 an exemplary trap bottle assembly 20 mounted on an exemplary conventional suction regulator or controller 10. In this case the suction regulator or controller 10 is a Model 3930, sold by Boehringer Laboratories, Inc., the assignee of the subject invention. It should be noted that the trap bottle assembly 20, is suitable for mounting or other suction regulators or controller of Boehringer Laboratories with little or no modification, and can be mounted on other manufacturer's prior art suction regulators or controller with minor modification.

Before discussing the details of the trap bottle assembly 20, a brief description of the exemplary suction regulator or controller 10 is in order. To that end, as can be seen that it basically comprises a housing 12 including various internal regulating components (whose details will not be described since they are not relevant to the subject invention), a suction adjusting knob 14, a mode selector knob 16, and a linear gauge 18. The suction adjusting knob 14 is a rotary knob which is used to establish the desired amount of suction to be provided by the regulator or controller, depending upon the rotary position of that knob. To that end, rotation of the knob 14 in the counter-clockwise direction increases the suction setting, whereas rotation of the knob in the clockwise direction decreases the suction setting. The suction adjusting knob 14 is coupled to various internal components, e.g., a spring biased diaphragm assembly shown in FIG. 8, within the housing 12 for precisely controlling the suction applied to the patient circuit.

The mode selector knob 16 is coupled to a mode selector valve located within the housing 12 as shown in FIG. 1, and is provided to set the regulator into the desired operating mode. Depending upon the particular suction regulator or controller, there can be various operating modes. One mode is the "OFF" mode wherein suction is off. Another mode is the "REG" mode wherein the suction provided to the regulator or controller from the central suction system via a wall connector (the "wall suction") is controlled to the specific level as set by the position of the suction adjusting knob 14 and delivered to the patient collection system. Another mode is the "LINE" mode wherein the regulating mechanism of the suction regulator or controller is bypassed, such that full wall suction is applied to the patient collection system. Still another mode is the "INTERMIT" mode wherein when suction regulator or controller is in this mode regulated suction to the patient collection system is intermittently turned on and off (e.g., vented to the atmosphere). Yet another mode is the "CONTIN" mode. In that mode suction is continuous and is controlled to the specific level established by the suction adjusting knob. Thus, the "CONTIN" is similar to the "REG" mode.

The linear gauge 18 provides a visual indication of the amount of suction provided by the suction regulator or controller 10 and is coupled to various internal components within the housing 12. In particular, the gauge 18 allows accurate readings from a 180 degree field of view, does not require calibration and is color coded to identify particular suction ranges.

Figure 2:
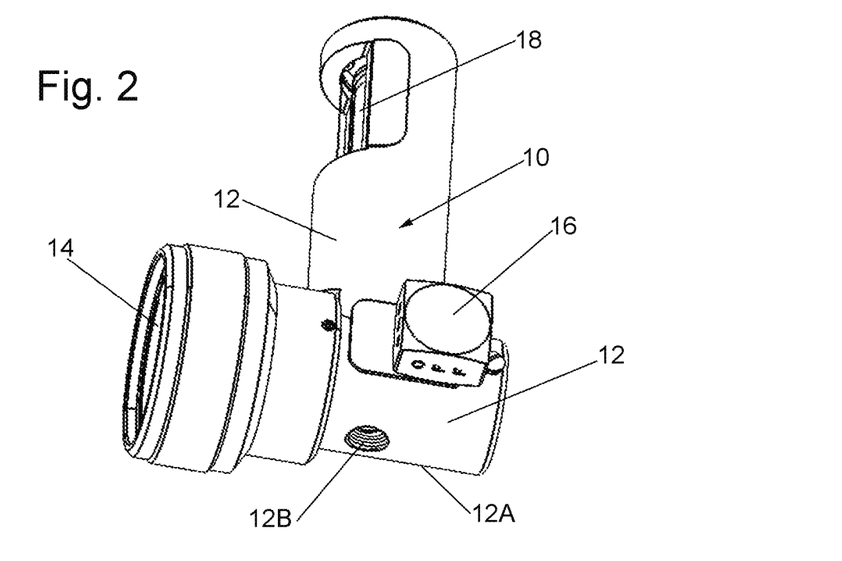
FIG. 2 is an enlarged isometric view of the suction regulator or controller shown in FIGS. 1A and 1B.

As best seen in FIG. 2 the bottom of the housing 12 includes an arcuate surface 12A into which an internally threaded bore 12B extends. The bore 12B is in fluid communication with the interior of the housing and various components therein. Moreover, the bore 12B serves to receive a threaded tubular connector (to be described shortly) of the trap bottle assembly 20 to mount that assembly onto the regulator or controller 10.

Figures 3, 4:
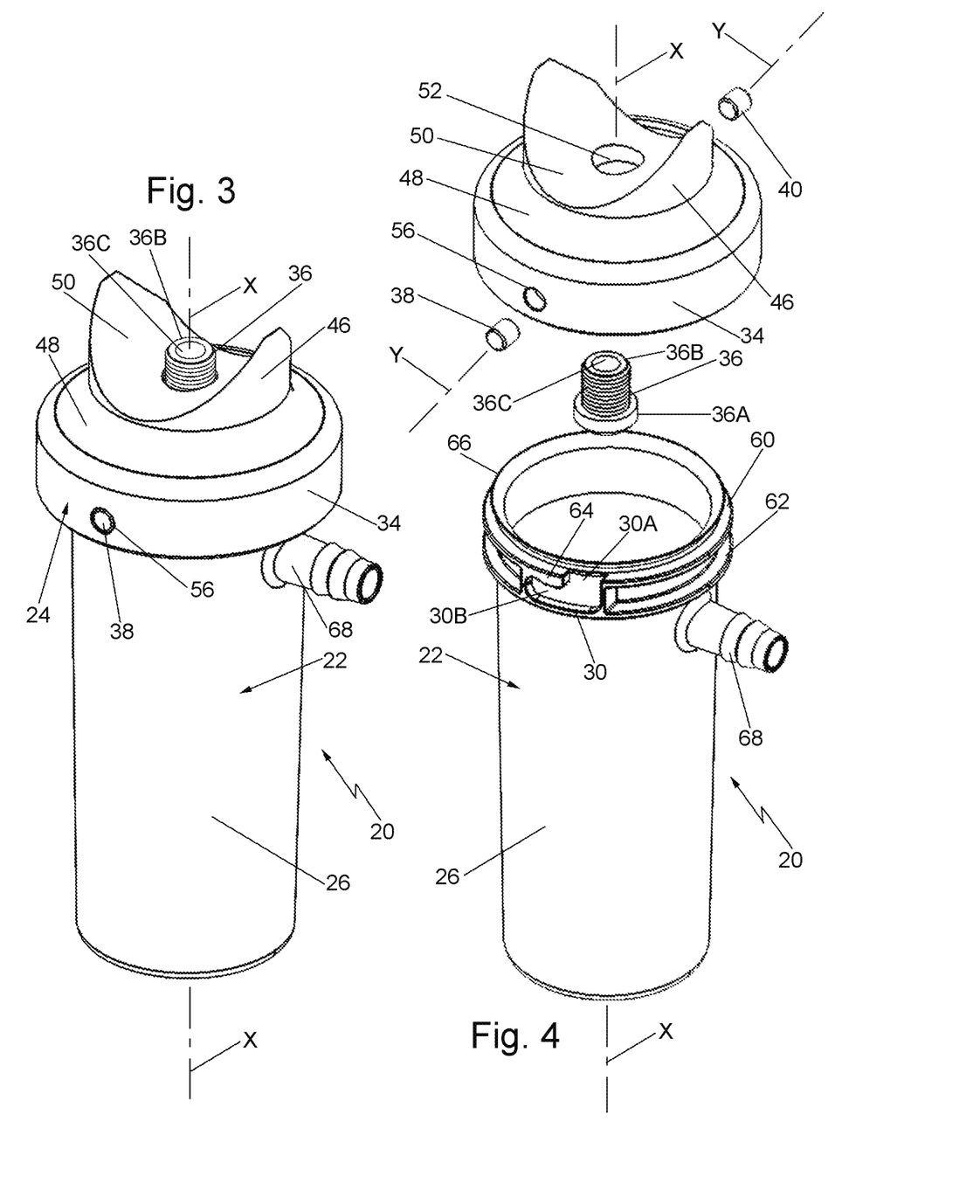
FIG. 3 is an enlarged isometric view of the trap bottle assembly shown in FIGS. 1A and 1B.
FIG. 4 is an enlarged exploded isometric view of the trap bottle assembly shown in FIG. 3.
Figure 7A:
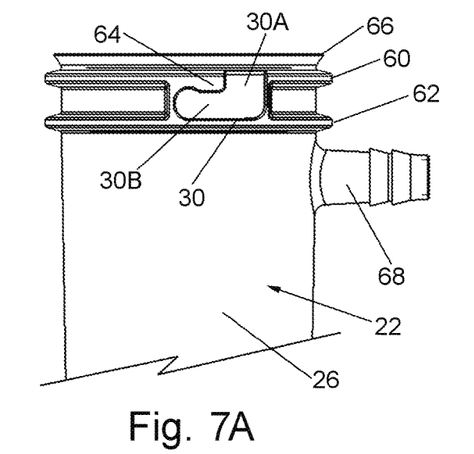
FIG. 7A is a left side elevation view of a portion of another component, i.e., a trap bottle of the trap bottle assembly of FIG. 3.
Figure 7B:
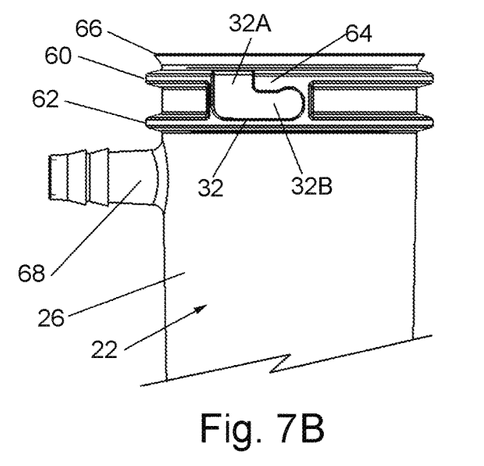
FIG. 7B is a right side elevation view of a portion of the trap bottle shown in FIG. 7A.
Figures 7C, 7D, 7E:
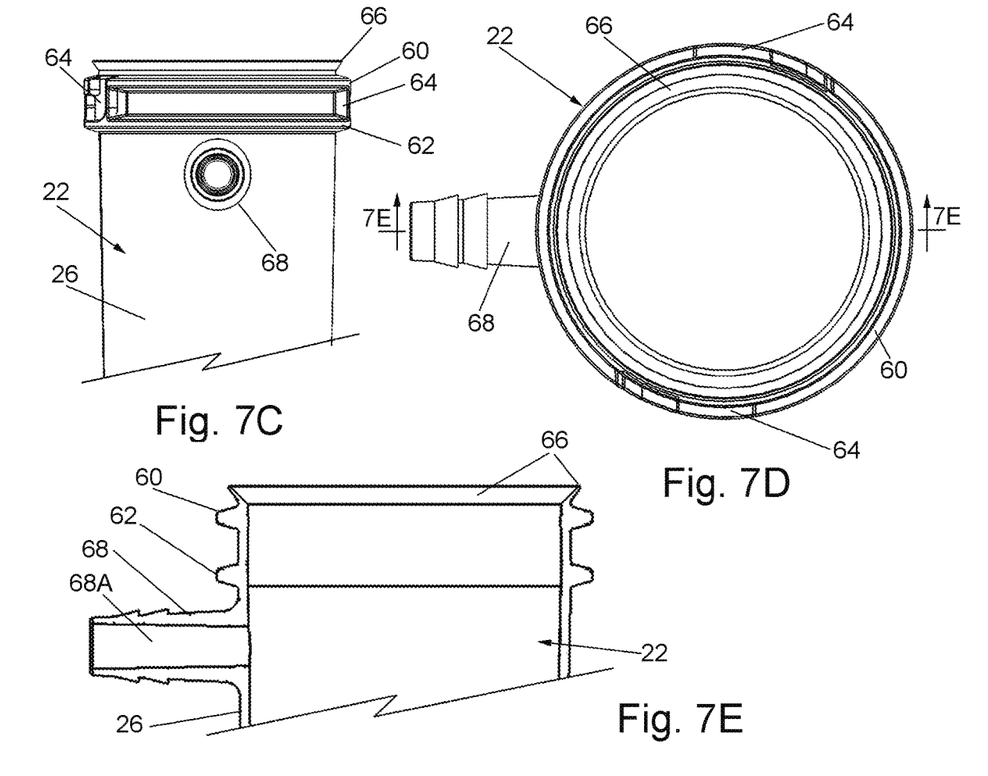
FIG. 7C is a front side elevation view of the portion of the a trap bottle shown in FIGS. 7A and 6B.
FIG. 7D is an enlarged top plan view a the portion of the trap bottle shown in FIGS. 7A-7C.
FIG. 7E is a sectional view taken along line 7E of FIG. 7D.
Figure 8:
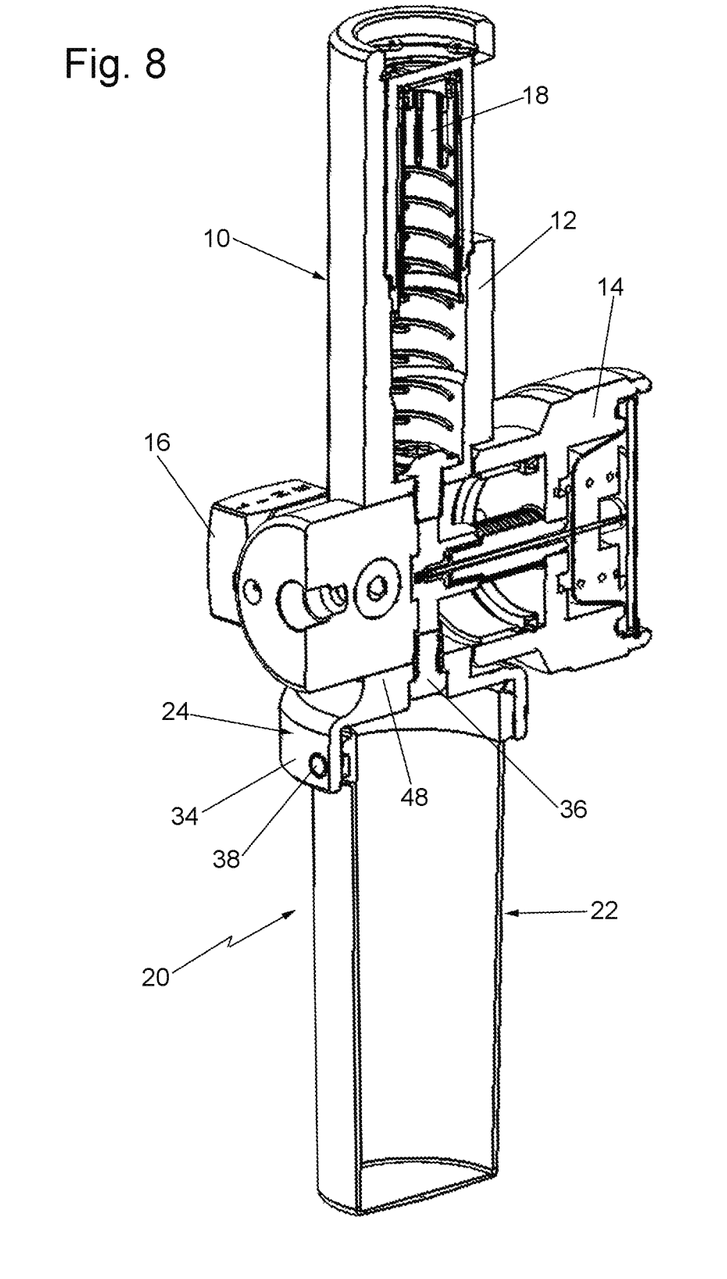
FIG. 8 is an isometric view, partially in section, of the suction regulator or controller with a trap bottle assembly of the subject invention releasably mounted thereon.

The trap bottle assembly 20 is best seen in FIGS. 3, 4 and 8. Thus, as can be seen it basically comprises a trap bottle 22 and a mounting adaptor 24. The trap bottle 22 will be described in detail shortly. Suffice it for now to state that it is a hollow cup-cup shaped member having a circular sidewall 26 extending about a longitudinal central axis X. The top portion 28 of the sidewall 26 includes two diametrically opposed general L-shaped slots 30 and 32 (FIGS. 4, 7A and 7B). The slots 30 and 32 are configured to receive respective pins (to be described shortly) of the mounting adaptor 24 to form a bayonet connection for releasably mounting the trap bottle 22 to the mounting adaptor 24.

The mounting adaptor 24 is preferably a non-disposable subassembly of components that is configured to be secured to the suction regulator or controller 10, where it will typically be left in place for releasably mounting a trap bottle 22 thereon. The trap bottle 22, itself, is a disposable unit, which after use is discarded, leaving the mounting adaptor in place on the suction regulator or controller for mounting another (new) trap bottle thereon. The mounting adaptor 24 can be formed of any suitable material, e.g., aluminum, and basically comprises a body member 34. It also includes the threaded tubular connector mentioned above, now identified by the reference number 36, and the heretofore mentioned pins, now identified by the reference numbers 38 and 40. Thus, the mounting adaptor can be thought of as a subassembly of components which when assembled forms an integral unit for connection or mounting on the suction regulator or controller.

Figure 5A:
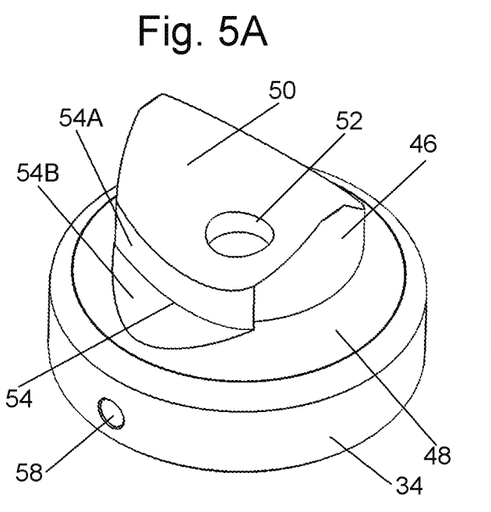
FIG. 5A is an enlarged isometric view of one component, i.e., the body member, of the trap bottle assembly of FIG. 3 taken from an oblique angle above the component.
Figure 5B:
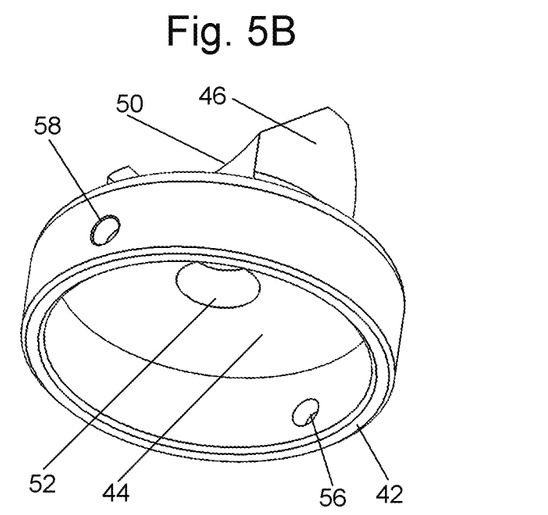
FIG. 5B is an enlarged isometric view of the body member of the trap bottle assembly of FIG. 3 taken from an oblique angle below the component.
Figure 5C:
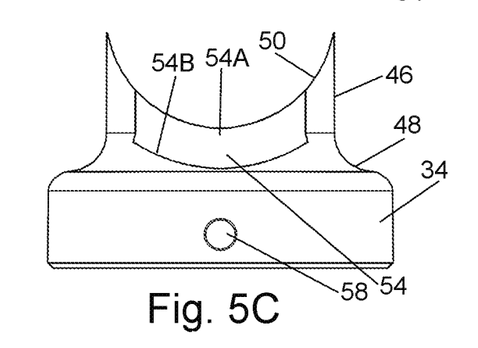
FIG. 5C is a front side elevation view of the body member of the a trap bottle shown in FIGS. 5A and 5B.
Figure 5D:
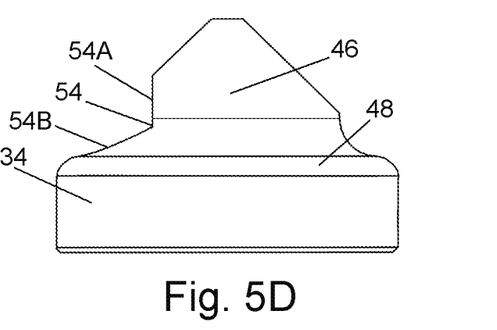
FIG. 5D is a left side elevation view of the body member of the a trap bottle shown in FIGS. 5A and 5B.
Figure 5E:
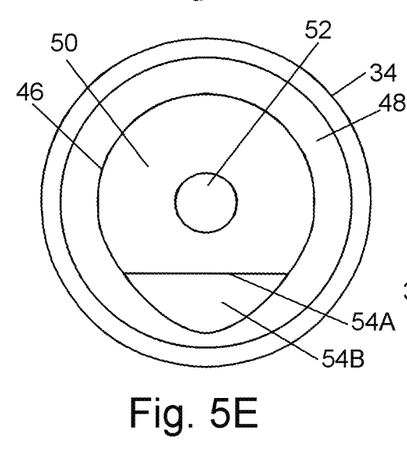
FIG. 5E is a top plan view of the body member of the a trap bottle shown in FIGS. 5A and 5B.
Figures 6A, 6B, 6C:
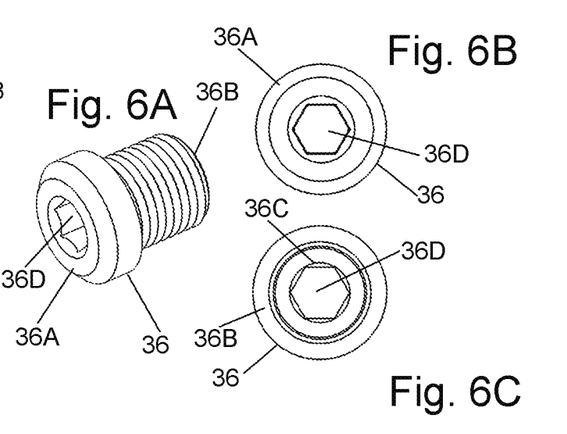
FIG. 6A is an enlarged isometric view of one component, i.e., the threaded tubular connector, of the trap bottle assembly of FIG. 3.
FIG. 6B is a bottom plan view of the threaded tubular connector shown in FIG. 6A.
FIG. 6C is a top plan view of the threaded tubular connector shown in FIG. 6A.

As best seen in FIG. 5B the bottom of the body member 34 is in the form of a circular peripheral sidewall 42 bounding a planar undersurface 44. The top of the body member 34 is in the form of a cylindrical projection 46 (FIGS. 3, 4 and 5A-5D) extending up from an intermediate section 48 of the body member. The intermediate section is located between the sidewall 42 and the projection 46. The projection 46 is centered about the longitudinal central axis X and includes a semi-circular arcuate recess 50 extending from the top of the projection downward toward the intermediate section 48. A clearance bore or hole 52 extends through the body portion 46 from nadir of the recess 50 to the undersurface 44 of the body member. A notch 54 is provided in a portion of the projection 46 and a contiguous portion of the intermediate section 48. The notch 54 is provided to receive a portion of the rotary suction adjusting knob 14 when the trap bottle assembly 20 is mounted on the suction regulator or controller 10. To that end, the notch 54 includes a planar surface portion 54A in the projection 46 and an arcuate surface portion 54B in the intermediate section 48. The arcuate surface portion 54B is in the form of a sector of a circle whose radius of curvature is slightly greater than the radius of curvature of a portion of the rotary suction adjusting knob 14 so that a portion of the rotary suction adjusting knob can readily fit within the notch 54 when the trap bottle assembly 20 is mounted on the suction regulator or controller.

The threaded tubular connector 36 is best seen in FIGS. 4 and 6A-6C. Thus as can be seen the connector 36 is a tubular member having a head end 36A, a tail end 36B and a central passageway 36C extending between the head and tail ends. The outer surface of the tubular member from the head end to the tail end is externally threaded. The end of the passageway 36 of the threaded tubular connector at the head end thereof is in the form of a hex-shaped socket 36D. The socket 36D is configured to receive a hex head tool (not shown) to secure the mounting adaptor 24 to the suction regulator or controller 10 as will be described later.

As mentioned earlier the trap bottle 22 is configured to be releasably connected, via a bayonet-type connection, to the mounting adaptor 24. To that end, as best seen in FIGS. 3, 4, and 5A-5C the mounting adaptor includes two diametrically opposed apertures 56 and 58, for receipt of the pins 38 and 40. When the pins are located within those apertures the inner or free ends of the pins extend radially inward beyond the inner surface of the sidewall 42 of the body member 34. The extending free end of pin 38 is configured to be received within the L-shaped slot 30 of the trap bottle 22 and the extending free end of the pin 40 is configured to be received within the L-shaped slot 32 to releasably mount the trap bottle 22 to the mounting adaptor 24 (which is in turn secured to the body 12 of the suction regulator or controller as described above).

Turning now to FIGS. 7A-7E the details of the trap bottle will now be descried. As mentioned earlier the trap bottle 22 is a hollow cup-cup shaped member designed for disposal after use. Thus, it can be formed of any suitable material, e.g., low density polyethylene. The trap bottle has a circular sidewall 26 extending about a longitudinal central axis X. The outer surface of the top portion 28 of the sidewall 26 includes two annular flanges 60 and 62 projecting outward from the outer surface. A thickened wall region 64 is located between the annular flanges 60 and 62. One of the thickened wall regions 64 serves as the location for the L-shaped slot 30, while the other of the thickened wall regions 64 serves as the location for the L-shaped slot 32. The L-shaped slot 30 includes a first or entryway slot section 30A (FIG. 7A) extending parallel to the longitudinal central axis X and a second slot section 30B merging with the first slot section 30A. The slot section 30A extends parallel to the longitudinal central axis X, while the slot 30B extends perpendicularly to the slot section 30A. In a similar manner the L-shaped slot 32 includes a first or entryway slot section 32A (FIG. 7A) extending parallel to the longitudinal central axis X and a second slot section 32B merging with the first slot section 32A. The slot section 32A extends parallel to the longitudinal central axis X, while the slot 32B extends perpendicularly to the slot section 32A.

The top or lip of the sidewall 26 is best seen in FIGS. 7A-7E and is in the form of a tapering annular flange 66 which projects upward and outward at an acute angle. The tapering shape of the flange 66 and the material making up the trap bottle, e.g., the low density polyethylene, enables the flange to deflect or bend when the trap bottle is secured to the mounting adaptor to form a good fluid-tight interface or seal therebetween. In particular, when the trap bottle is releasably secured to the mounting adaptor, as will be described shortly, the annular flange 66 will engage the planar undersurface 44 of the body member to flex slightly and form a good fluid-tight interface or seal between the flange and the undersurface.

It should be pointed out at this juncture that while the annular flange 66 is shown and described as tapering and extending upward and outward at an acute angle, that configuration is merely exemplary. Thus, for example, the flange need not taper, so long as it flexes to tightly engage the undersurface of the body member to form a good, fluid-tight seal therebetween.

The securement or mounting of the mounting adaptor 24 onto the suction regulator or controller 10 and the subsequent mounting of the trap bottle 22 onto the mounting adaptor 24 will now be described. To that end, the mounting adaptor 24 is connected to the suction regulator or controller 10 by juxtaposing the mounting adaptor so that the arcuate recess 50 of its body member 34 confronts the arcuate surface 12A of the body 12 of the suction regulator or controller 10, and with the threaded tail end 36B of the tubular connector 36 axially aligned with the entrance to the internally threaded bore 12B. A hex-head tool can then be inserted into the hex-shaped socket 36D to screw the tubular threaded member 36 into the internally threaded bore 12B until the surface of the recess 50 in the body member engages the portions of the body portion 12A that is contiguous with the bore 12B. That action completes the securement of the mounting adaptor 24 to the suction regulator or controller.

With the mounting adaptor 24 secured to the suction regulator or controller 10, the trap bottle 22 can be releasably secured to the mounting adaptor. That action is accomplished by juxtaposing the pin 38 adjacent one of the L-shaped slots 30 or 32 of the trap bottle, while the pin 40 is adjacent the other of the L-shaped slots of the trap bottle, so that the free end of the pins enter the first sections of the slots. For example, if pin 38 is located adjacent the L-shaped slot 30, the trap bottle 22 is moved along axis X so that the free end of the pin 38 enters into the entryway section of 30A of the slot 30. At the same time the free end of the pin 40 will enter into the entryway section 32A of the slot 32. Once the free end of those pins reach the ends of the slot sections 30A and 32A, the trap bottle can be rotated in the clockwise direction to cause the free end of those pins to enter and slide down the contiguous slot sections 30B and 32B until they reach the end of those slot sections. This action establishes a bayonet-type releasable connection between the trap bottle and the mounting adaptor, and with the annular flange 64 flexed and in tight engagement with the undersurface 44 of the body member 34 to form the heretofore described seal.

The sidewall 26 of the trap bottle includes a barbed tubular connector 68 that is located slightly below the annular ring 62 and which extends radially outward. The connector 68 includes a central passageway 68A that is in fluid communication with the interior of the trap bottle 22. The outer surface of the connector 68 is barbed and configured to be tightly received within one end of a section of flexible tubing 70 having a conventional connector 72 at its opposite end. The connector is configured to be connected to the patient system for which suction is to be controlled. For example, if the suction regulator or controller 10 with the trap bottle assembly 20 of this invention mounted thereon is used with a heart-lung perfusion apparatus (not shown) the flexible tubing 70 from the connector 68 will be coupled to that apparatus via the connector 72. Thus, when the suction regulator or controller is mounted on the wall suction port of the hospital's suction system, suction will be applied via the regulator or controller into the interior of the trap bottle via the passageway 36C of the tubular connector, and from whence through the barbed connector 68 to the flexible tube connected to that connector. Any moisture, blood or other body fluids will thus flow into the trap bottle 22 for collection and to prevent it from entering into the interior of the regulator or controller. The flexible tubing 70 can be made of any suitable material, e.g., polyvinylchloride ("PVC") of 0.250 inch inside diameter and 0.385 outside diameter. The connector 72 can also be made of any suitable material, e.g., PVC.

It should be noted at this juncture that the subject invention can be used for any application wherein suction is to be applied from a suction regulator or controller to a patient circuit, and where fluids are to be collected and trapped within the trap bottle. Thus, the above description of the use of the subject apparatus with a heat-lung apparatus is merely exemplary.

Without further elaboration the foregoing will so fully illustrate our invention that others may, by applying current or future knowledge, adopt the same for use under various conditions of service.

We claim:

1. A trap bottle assembly for releasable mounting on a suction regulator or controller, said trap bottle assembly comprising:
   a trap bottle, said trap bottle being a hollow member having a bottom wall, and a peripheral side wall, said peripheral side wall having a top portion including a circular top surface from which a circular annular flange or lip projects upward at an acute angle, said circular annular flange or lip being configured to deflect or bend; and
   a mounting adaptor, configured for releasable securement to a portion of the suction regulator or controller, said mounting adaptor comprising a body member and a threaded tubular connector, said body member having a peripheral circular sidewall surrounding a planar undersurface, said planar undersurface including a bore, said tubular connector having a central passageway extending therethrough, a peripheral sidewall, and a flanged head projecting outward from said peripheral sidewall, said peripheral sidewall being externally threaded, said externally threaded sidewall being configured for receipt within an internally threaded bore in the suction regulator or controller, whereupon said flanged head of said tubular connector engages a portion of said planar undersurface contiguous with said bore to releasably secure said mounting adaptor to said portion of the suction regulator or controller, said peripheral circular sidewall being configured to receive and releasably mount said top portion of said sidewall of said trap bottle to said mounting adaptor, whereupon said circular annular flange or lip of said trap bottle tightly engages said planar undersurface of said body member immediately adjacent said peripheral circular sidewall along the entire circumference of said peripheral circular sidewall to cause said annular flange or lip of said trap bottle to deflect or bend and form a fluid tight interface between said undersurface of said body member and said circular annular flange or lip of said trap bottle when said trap bottle is releasably secured to said mounting adaptor.

2. The trap bottle assembly of claim 1, wherein said body member includes a first pin projecting inward from said sidewall thereof, said first pin being configured for receipt within a first slot located at said top portion of said peripheral sidewall of said trap bottle to releasable mount said trap bottle on said mounting adaptor.

3. The trap bottle assembly of claim 2, wherein said trap bottle includes a longitudinal central axis about which said peripheral sidewall of said trap bottle extends, and wherein said first slot comprises a first slot section extending parallel to said longitudinal central axis and a second slot section extending perpendicular to said longitudinal central axis, said first slot section being in communication with said second slot section, said first slot section being configured to receive said first pin and enable said trap bottle to be manipulated so that said first pin slides down said first slot section to said second slot section, whereupon rotation of said trap bottle about said longitudinal central axis causes said first pin to enter in said second slot section, thereby releasably mounting said trap bottle on said mounting adaptor.

4. The trap bottle assembly of claim 3, wherein said mounting adaptor includes a second pin, wherein said trap bottle includes a second slot located at said top portion of said peripheral sidewall of said trap bottle and configured for receipt of said second pin, said second slot comprising a first slot section configured to receive said second pin and enable said trap bottle to be manipulated so that said second pin slides down said first slot section of said second slot to said second slot section of said second slot, whereupon rotation of said trap bottle about said longitudinal central axis causes said second pin to enter in said second slot section of said second slot, thereby releasably mounting said trap bottle on said cap and connector assembly mounting adaptor.

5. The trap bottle assembly of claim 1, wherein said tubular connector includes an inner end which is open to said central passageway and a slot into which a tool can be inserted to screw said tubular connector into the internally threaded bore of the suction regulator or controller to releasably mount said trap bottle assembly on the suction regulator.

6. The trap bottle assembly of claim 1, wherein the suction regulator or controller includes a housing portion having an arcuate surface and into which the internally threaded bore extends, and wherein said body member of said mounting adaptor includes a projection having a first arcuate recess therein, said first arcuate recess being configured to receive said arcuate surface of the housing portion when said trap bottle assembly is mounted on the suction regulator or controller.

7. The trap bottle assembly of claim 6, wherein the suction regulator or controller includes a knob projecting outward from the housing portion adjacent the arcuate surface, and wherein said projection includes a second recess located adjacent said first arcuate recess, said second recess being configured to receive the knob when said trap bottle assembly is mounted on the suction regulator or controller.

8. The trap bottle assembly of claim 4, wherein said tubular connector includes an inner end which is open to said central passageway and a slot into which a tool can be inserted to screw said tubular connector into the internally threaded bore of the suction regulator or controller to releasably mount said trap bottle assembly on the suction regulator.

9. The trap bottle assembly of claim 4, wherein the suction regulator or controller includes a housing portion having an arcuate surface into which the internally threaded bore extends, and wherein said body member of said mounting adaptor includes a projection having a first arcuate recess therein, said first arcuate recess being configured to receive said arcuate surface of the housing portion when said trap bottle assembly is mounted on the suction regulator or controller.

10. The trap bottle assembly of claim 9, wherein the suction regulator or controller includes a knob projecting outward from the housing portion adjacent the arcuate surface, and wherein said projection includes a second recess located adjacent said first arcuate recess, said second recess being configured to receive the knob when said trap bottle assembly is mounted on the suction regulator or controller.

* * * * *